Figure 1:
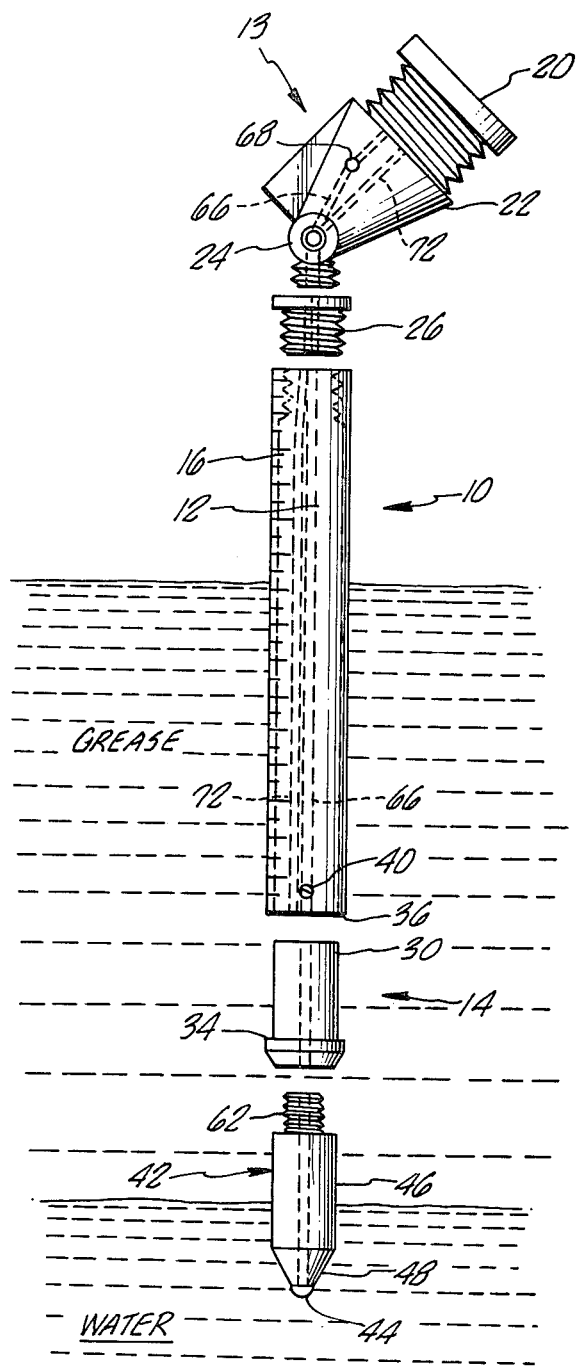

United States Patent [19]

Keefner et al.

[11] 4,266,195
[45] May 5, 1981

[54] WATER DETECTOR

[76] Inventors: Eugene F. Keefner, 12009 E. 95th St., Cerritos, Calif. 90801; John R. Keefner, 616 Delaware Ave., Huntington Beach, Calif. 92648

[21] Appl. No.: 973,717

[22] Filed: Dec. 27, 1978

[51] Int. Cl.³ .......................................... G01N 27/02
[52] U.S. Cl. ................................. 324/439; 324/61 P; 324/65 P
[58] Field of Search ............... 324/65 P, 61 P, 65 R, 324/437, 425, 439, 446

[56] References Cited

U.S. PATENT DOCUMENTS

| 1,910,021 | 5/1933 | Legg | 324/65 P |
| 3,133,437 | 5/1964 | Remke et al. | 324/61 P |
| 3,178,901 | 4/1965 | Blackett | 324/65 P |
| 4,052,667 | 10/1977 | Schwartz | 324/65 P |

OTHER PUBLICATIONS

Renderer, (Advertisement), Oct. 1978, p. 30.

Primary Examiner—Michael J. Tokar
Attorney, Agent, or Firm—Lyon & Lyon

[57] ABSTRACT

An apparatus and method for detecting the presence of water in a non-conductive medium such as liquid or solid grease are described. The apparatus utilizes the electrochemical potential difference of two metals, and includes an integral grounding element.

15 Claims, 2 Drawing Figures

U.S. Patent    May 5, 1981    4,266,195

WATER DETECTOR

BACKGROUND

Detecting the presence of water in media which are substantially electrically non-conductive such as grease and oil is a difficult problem, and particularly to the food, the petrochemical and rendering industries. In the rendering industry, a prime source of raw materials is grease and oils produced as by-products by other industries such as the grease produced by restaurants. This grease is often contaminated with water, sometimes intentionally added. It is important to determine how much water is in the grease so that renderer does not pay unnecessarily for a valueless raw material, namely water.

The technique most commonly used by the rendering industry for detecting the presence of water in grease is insertion of a "trier", a hollow sampling tube, into a container of the grease. The trier is withdrawn from the container, bringing with it layers of grease and water. With a trier, continuous layers and sometimes pockets of water can be detected. However, it is very difficult to accurately determine the thickness of water layers and to locate small pockets of water with a trier.

Therefore, there is a need for an easy-to-use, accurate, and inexpensive water-in-grease detector and measuring device. It is important that the device be inexpensive because it is desirable that the apparatus be used as a replacement for the trier on practically every grease collection truck in the nation, which includes thousands of trucks.

SUMMARY

The present application is directed to a water-in-grease detector with the above features. The detector comprises a first element having a first electrochemical potential and a second element in electrical contact with the first element and having an electrochemical potential different from the first electrochemical potential. Means for measuring current when at least a portion of the second element is in water and the first element is in medium which is substantially electrically non-conductive medium are also provided. The grounding element is integrally attached to and supported by the second element. The grounding element is electrically insulated from the first and second elements and is electrically connected to the measuring means.

It is an important feature of the present invention that the grounding element is integral with the second element. This is because prior art devices which have been used for determining the water level in petroleum industry oil tanks have a grounding element which is attached to the wall of the tank. Although this is satisfactory in the oil industry where practically all tanks are made of metal, it is unsatisfactory for the rendering industry where many grease containers are made of non-conductive plastic material.

The detector is relatively simple to use. It is used by inserting the grounding element, the first element and the second element into a container containing grease and monitoring the measuring means for an indication of current generation. Such current generation indicates that at least a portion of the second element is in water.

DRAWINGS

Figure 2:
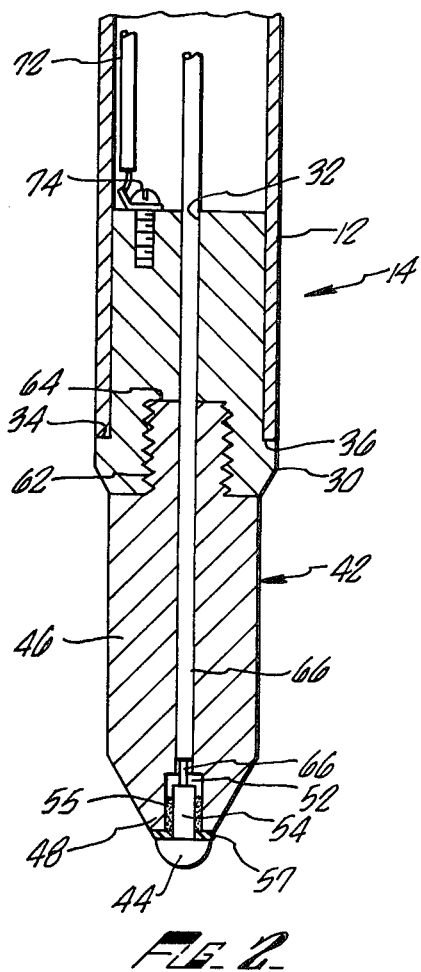

These and other features, aspects and advantages of the present invention will be become better understood with reference to the following description, appended claims, and accompanying drawings where:

FIG. 1 is a front elevation view, partially exploded, of an apparatus embodying features of the present invention; and FIG. 2 is a sectional view of the sensing element of the apparatus of FIG. 1

DESCRIPTION

With reference to FIG. 1, a water-in-grease detector 10 embodying features of the present invention comprises an elongated hollow barrel 12 having mounted at one end a current meter assembly 13 for detecting an electrical current and mounted at the opposite end a water sensing unit 14. The water sensing unit 14 is shown in detail in FIG. 2. The barrel 12 has calibration markings 16 along its length so that the length to which the sensing element is inserted into a container can be determined.

The current meter assembly 13 comprises a meter 20 mounted in a meter housing 22 that is swivelly connected to the barrel 12 by a swivel connector 24 screwed into a bushing 26. The bushing is screwed into a threaded inner portion of the barrel 12.

Since very little current is generated by the sensing unit 14, preferably a very sensitive meter 20 is used. The preferred meter used is Model No. 150-W/UADC manufactured by International Meter Co. of Orange, Connecticut, having a resistance of 1/10th of a megohm.

It is desirable that the meter be swivelly connected to the barrel so that the operator can easily note movement of the meter needle. The meter face preferably has three areas marked in contrasting colors, such as a white area, a green area, and a red area. In a preferred version of the present invention, when the needle is at zero, this indicates that no moisture is being detected. When the needle moves into the white area, this indicates the sensing element is detecting measurable moisture. When the needle is in the green area, this indicates that the sensing unit has encountered pockets of entrapped moisture in the grease or a higher concentration of water. When the needle moves into the red portion of the meter dial, this indicates that the sensing unit has encountered a solid layer. Due to the calibrations 16 along the length of the barrel 12, by a simple calculation an operator can determine how much water is present in the container. The meter does not necessarily have a needle indicator, but instead can provide digital readout.

The sensing element 14 comprises a cylindrical metallic insert 30 having an axially oriented cylindrical path 32, the path being in communication with the hollow central portion of the barrel 12. The insert 30 is mounted inside of the barrel. The insert 30 has a circumferential shoulder 34 which seats against the base 36 of the barrel 12. The insert is pressed into the barrel and is held securely in place by a close tolerance fit and an adhesive such as Loctite ® 277-31 high strength adhesive sealant made by Loctite of Newington, Connecticut.

The sensing element 14 also includes a nose-piece 42 and a grounding element 44. The nose-piece 42 has a cylindrical body portion 46 and a conical nose portion 48 with the grounding element 44, which is preferably is a rivet, mounted at the apex of the conical portion 48. A recess 52 is provided at the apex of the nose-piece for the shaft 54 of the rivet 44. The rivet 44 is held in place in the recess 52 by means of an electrically non-conductive sealant 55 such as high tensile strength epoxy resin having the tradename Chemweld manufactured by Seatex of Houston, Texas. Thus, the rivet 44 is electrically insulated from both the nose-piece 42 and the insert 30. In addition to the epoxy 55 that is used to hold the rivet 44 in place in the recess 52 of the nose-piece 42, the rivet is insulated from the nose piece 42 by an insulating washer 57 made of electrically non-conductive material such as fiber, plastic, nylon, or other suitable material, and preferably teflon.

The cylindrical portion 46 of the nose-piece has a threaded extension 62 which is screwed into a correspondingly threaded recess 64 at the base of the insert 30. Thus, the insert and the nose-piece are in electrical contact. The nose-piece has a pathway 66 extending along its length from the recess 52 in which the rivet 50 is mounted through the threaded extension 62. This pathway 66 is aligned with the pathway 32 through the insert.

An insulated electrical wire 66 extends through these aligned pathways 32 and 66 and is electrically terminated by means of a solder connection to the rivet 54 at one end and to a solder connector 68 at the other end, the connector 68 being electrically terminated to the ground terminal (not shown ) of the electric meter.

Another solder and mechanical connection is made to the meter by means of a second insulated wire 72. The second wire extends through the barrel and is connected at its opposite end to the insert 30 by means of a screw 74 and solder.

Preferably all the components of the detector 10 are made of corrosion resistant materials which are unaffected by grease or any other solvents for which the detector is used.

The choise of materials for the insert and the nose-piece is important to the functioning of the detector 10. These elements must be fabricated of materials having different electrochemical potentials. Preferably, the more electrochemically different the materials are, the most current generated and the more accurate and sensitive is the detector 10. By reference to standard tables of electrochemical potentials of metals, it is possible to select the materials for the insert and nose-piece. Possible combinations of materials include magnesium/silver, magnesium/copper, magnesium/brass, magnesium/tin, magnesium/iron, aluminum/silver, aluminum/copper, aluminum/tin, zinc/silver, zinc/copper, zinc/brass, and zinc/tin. This list of materials is not intended to be inclusive, but only representative of combinations of materials which can be used. A preferred combination is magnesium and brass, with the nose-piece being made of magnesium and the insert being made of brass. These materials provide sufficient electrical current for detection by a sensitive meter, and have a long life in service due to their resistance to corrosion.

The grounding rivet is made of material which is a good conductor and does not corrode. Suitable materials are silver, gold, copper, and iron. The preferred material is copper, since copper rivets are readily available and inexpensive.

The detector shown in FIG. 1 is particularly useful for identifying and measuring the volume of pockets and layers of water in a container of grease. It is sturdy, easy to handle, and relatively simple to insert into a container of grease even in cold weather when the grease is solidified. The detector 10 is accurate. It can be used with non-conductive containers, including containers made of plastic. It is self-contained and does not require a separate grounding wire mechanism. Because the grounding element is integral with the barrel, there is little chance that it can break off from the rests of the detector 10. Due to its simple construction, it is easy to fabricate and can be manufactured inexpensively.

The detector 10 is very simple to use. All that is necessary is that the sensing element 14 be inserted into a container containing water and an electrically non-conductive medium such as grease. The operator then monitors the meter 20 for an indication of current generation, the presence of such current indicating that at least a portion of the nose-piece in water. For example, with reference to FIG. 1, the grounding element 44 and the conical portion 48 of the nose-piece 42 are in a layer of water, while the insert 30 and the cylindrical portion 36 of the nose-piece are in grease. The meter 20 therefore registers an electrical current.

The substantially electrically non-conductive medium can be solid, liquid, or gaseous. For example, the meter can be used with solidified grease, liquid grease, and other liquids such as crude oil, petrochemicals, and agricultural oils such as corn oil, sunflower oil, and the like. The gaseious medium can be air. For example, the detector, with a long barrel 12 can be used for determining the water level in wells.

Although the barrel 12 is particularly useful for pentrating a layer of solidified grease, for many applications no barrel 12 is needed. Exemplary of such applications is detection of water level in water wells; mines; oil wells; and storage tanks for petrochemicals, refined petroleum oil, and crude petroleum oil.

For such applications, all that is required is the sensing element 14, a meter, electrical connection between the grounding element 44 and the meter and the nose-piece and the meter, and means for determining how far into a container or well the sensing element 14 is located. Such means can be a sufficient length of calibrated wire or metallic tape or rope sufficiently strong for supporting the sensing element.

Although the present invention has been described in considerable detail with reference to certain versions thereof, other versions of the present invention are possible. For example, although use of the detector 10 has been described primarily for detecting water in grease by the rendering industry, the detector 10 is also suitable for detecting the presence of water in other media which are substantially electrically non-conductive such as petroleum based products. In addition, although the meter assembly 13 is shown as being physically attached to the barrel, it can be separate from the barrel provided that the mter be in electrical connection with the ground and the nose-piece. For example, each of many containers of grease and water can be provided with a sensing element 14, each sensing element 14 being eletrically connected to one centrally located meter assembly. Furthermore, the detector 10 is not limited to detecting the presence of water in electrically non-conductive media, but can be used for detecting other electrically conductive media in electrically non-conductive media.

Therefore, the spirit and scope of the appended claims should not necessarily be limited to the preferred verions described herein.

What is claimed is:

1. In an apparatus for detecting the presence of an electrically conductive liquid in a medium which is substantially electrically non-conductive, the apparatus comprising (a) a first element having a first electrochemical potential, (b) a second element in electrical contact with the first element, the second element having an electrochemical potential different from the first electrochmeical potential, and (c) means for measuring electrical current generated when at least a portion of the second element is in the electrically conductive medium and the first element is in the medium which is substantially electrically non-conductive, the improvement comprising a grounding element attached to and supported by the second element, the grounding element being electrically insulated from the first and second elements and being electrically connected to the measuring means.

2. The apparatus of claim 1 wherein the first element comprises brass and the second element comprises magnesium.

3. The apparatus of claim 1 or 2 in which the grounding element comprises copper.

4. The apparatus of claim 1 including means for supporting the grounding element, first element, and the second element in the substantially electrically non-conductive medium.

5. The apparatus of claim 4 in which the supporting means is calibrated along its length.

6. An apparatus for detecting the presence of pockets and layer of water in a container containing grease, including in plastic containers, comprising an elongated hollow barrel having mounted at one end means for detecting an electrical current and mounted at the opposite end a water sensing unit, the sensing unit comprising:
(i) an insert secured to the barrel, the insert having a first electrochemical potential and a path therethrough in communication with the inside of the barrel,
(ii) a nose-piece attached to the insert, the nose-piece having a second electrochemical potential different from the first electrochemical potential and a path therethrough in communication with the path through the insert,
(iii) a grounding element proximate to the tip of the nose-piece, said grounding element being electrically insulated from the insert and the nose-piece,
(iv) a first insulated conductive wire electrically connected at one end to the grounding element and electrically connected at the opposite end to the detecting means, the first wire passing through the path through the insert, the path through the nose-piece, and through the barrel, and
(v) a second insulated conductive wire electrically connected at one end to the insert and electrically connected at the opposite end to the detecting means, the second wire passing through the barrel.

7. The apparatus in claim 6 in which the insert comprises brass and the nose-piece comprises magnesium.

8. The apparatus of claims 6 or 7 in which the grounding element comprises copper.

9. The apparatus of claim 6 in which the first insulated conductive wire is electrically connected to the detecting means by a connector.

10. The apparatus of claim 6 in which the barrel is calibrated along its length.

11. A method for detecting the presence of pockets and layers of an electrically conductive medium in a medium which is substantially electrically non-conductive comprising the steps of:
(a) selecting an apparatus comprising (i) a first element having a first electrochemical potential, (ii) a second element in electrical contact with the first element, the second element having an electrochemical potential different from the first electrochemical potential, (iii) means for measuring electrical current generated when at least a portion of the second element is in the medium which is substantially electrically non-conductive, and (iv) a grounding element attached to and supported by the second element, the grounding element being electrically insulated from the first and second elements and being electrically connected to the measuring means;
(b) moving the grounding element, the first element, and second element of the apparatus toward the electrically conductive medium; and
(c) monitoring the measuring means of the apparatus for an indication of electrical current generation, the presence of such current indicating that at least a portion of the second element is in the electrically conductive medium water.

12. The method of claim 11 in which the container is formed of a material which is substantially electrically non-conductor.

13. The method of claim 11 in which the electrically conductive medium is water, the medium which is substantially electrically non-conductive is air, the water being at the bottom of a well, and the step of moving comprises lowering the first, second, and grounding elements down the well.

14. A method for detecting the presence of pockets and layers of water in a container containing a medium which is substantially electrically non-conductive comprising the steps of:
(a) selecting an apparatus comprising an elongated hollow barrel having mounted at one end means for detecting an electrical current and mounted at the opposite end a water sensing unit, the sensing unit comprising:
(i) an insert secured to the barrel, the insert having a first electrochemical potential and a path therethrough in communication with the inside of the barrel,
(ii) a nose-piece attached to the insert, the nose-piece having a second electrochemical potential different from the first electrochemical potential and a path therethrough in communication with the path through the insert,
(iii) a grounding element proximate to the trip of the nose-piece, said grounding element being electrically insulated from the insert and the nose-piece,
(iv) a first insulated conductive wire electrically connected at one end to the grounding element and electrically connected at the opposite end to the detecting means, the first wire passing through the path through the insert, the path through the nose-piece, and through the barrel, and
(v) a second insulated conductive wire electrically connected at one end to the insert and electrically connected at the opposite end to the detecting means, the second wire passing through the barrel;
(b) inserting the barrel, insert, nose-piece, and grounding element of the apparatus into the container; and
(c) monitoring the measuring means of the apparatus for an indication of electrical current generation, the presence of such current indicating that at least a portion of the nose-piece is in water.

15. The method of claim 14 in which the container is principally fabricated from plastic.

* * * * *